United States Patent
Fournie et al.

(10) Patent No.: US 9,814,551 B2
(45) Date of Patent: Nov. 14, 2017

(54) CANNULA AND ADAPTER FOR MULTIFUNCTION SYRINGE

(71) Applicant: PRODUITS DENTAIRES PIERRE ROLLAND, Merignac (FR)

(72) Inventors: Marguerite Fournie, Andernos-les-Bains (FR); Sabrina Saurou, Paris (FR)

(73) Assignee: PRODUITS DENTAIRES PIERRE ROLAND, Merignac (FR)

( * ) Notice: Subject to any disclaimer, the term of this patent is extended or adjusted under 35 U.S.C. 154(b) by 589 days.

(21) Appl. No.: 14/363,043

(22) PCT Filed: Nov. 26, 2012

(86) PCT No.: PCT/FR2012/052724
§ 371 (c)(1),
(2) Date: Jun. 5, 2014

(87) PCT Pub. No.: WO2013/083899
PCT Pub. Date: Jun. 13, 2013

(65) Prior Publication Data
US 2014/0342309 A1   Nov. 20, 2014

(30) Foreign Application Priority Data
Dec. 5, 2011   (FR) .................................. 11 61162

(51) Int. Cl.
*A61C 17/00* (2006.01)
*A61C 17/02* (2006.01)
(52) U.S. Cl.
CPC .......... *A61C 17/0202* (2013.01); *A61C 17/00* (2013.01)

(58) Field of Classification Search
CPC ... A61C 17/0202; A61C 17/00; A61B 5/6848; A61B 10/0275; A61B 2017/0445;
(Continued)

(56) References Cited

U.S. PATENT DOCUMENTS 1,531,213 A * 3/1925 Nimmer .............. A61M 3/0279
604/249
5,336,202 A    8/1994 Bailly et al.
(Continued)

FOREIGN PATENT DOCUMENTS

WO      90/07912 A1    7/1990
WO      92/04878 A1    4/1992

OTHER PUBLICATIONS

International Search Report from corresponding International PCT Application No. PCT/FR2012/052724, dated Mar. 14, 2013.

*Primary Examiner* — Yogesh Patel
(74) *Attorney, Agent, or Firm* — Workman Nydegger

(57) ABSTRACT

A cannula for a multifunction dental syringe includes a fastener bushing that is defined by a circular opening, an end wall, and a side wall comprising a circular cylinder. The cannula also includes at least two channels enabling fluids to be conveyed separately or together from the end wall to fluid projection orifices, and beginning in the end wall beside each other. The cannula is arranged so that the circular cylinder presents a cutout in the thickness of its wall. The cutout comprises, going from the opening, at least one segment extending in a direction other than the axial direction of the cylinder; followed by a longitudinal segment extending towards the end wall.

9 Claims, 3 Drawing Sheets

(58) Field of Classification Search
CPC ............ A61B 17/3462; A61B 17/3421; A61B 2017/3449; A61M 3/00–3/06
USPC .................................................. 433/80–90
See application file for complete search history.

(56) References Cited

U.S. PATENT DOCUMENTS

| | | | |
|---|---|---|---|
| 6,533,578 B2 | 3/2003 | Segal | |
| 6,796,796 B2 | 9/2004 | Segal | |
| 2001/0041321 A1* | 11/2001 | Segal | A61C 17/0202 433/19 |
| 2003/0190581 A1 | 10/2003 | Segal | |
| 2009/0317758 A1* | 12/2009 | Duineveld | A61C 17/0202 433/85 |
| 2015/0313635 A1* | 11/2015 | Jamali | A61B 17/3423 600/204 |

* cited by examiner

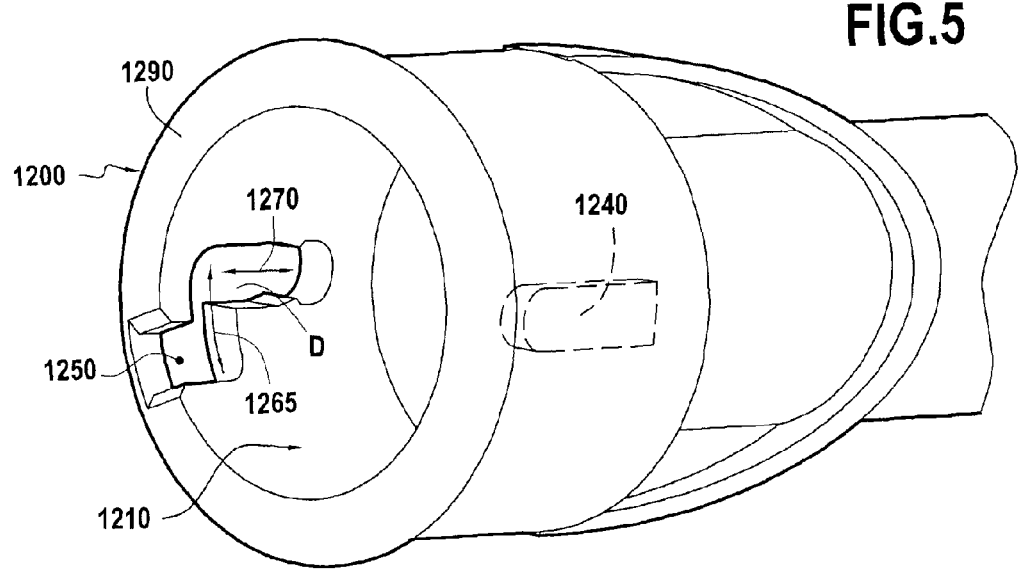
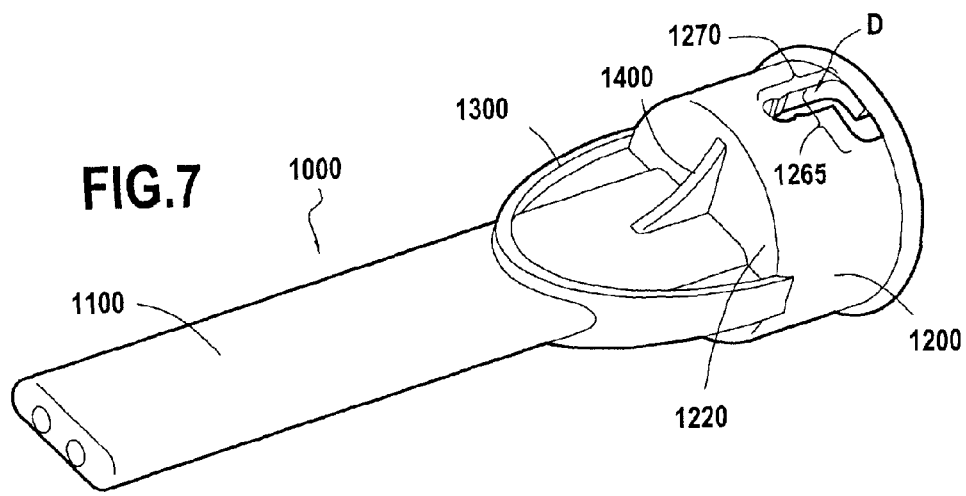
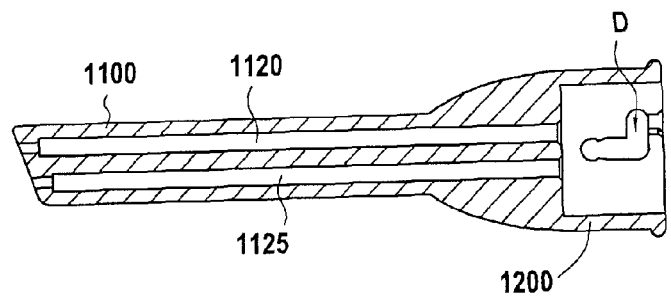

CANNULA AND ADAPTER FOR MULTIFUNCTION SYRINGE

TECHNICAL FIELD AND PRIOR ART

The invention lies in the field of equipment and appliances for dentistry.

Dentists' offices are commonly fitted with dentists' chairs that incorporate numerous instruments that are within reach of the practitioner while leaning over the patient. Among these instruments, a central element of the equipment is a syringe for projecting air, water, and an air/water mixture (multifunction syringe or air/water syringe).

The function of the air/water syringe is to deliver a constant stream of the selected fluid or fluid mixture so as to enable the practitioner to rinse and dry zones in the mouth depending on how the practitioner's intervention is proceeding. When the air-only function of the syringe is used, it is particularly important for the blown air to be completely dry, so as to guarantee good quality for the intervention.

Depending on the manufacturer of the dentists' chair, various different air/water syringes are in existence. These syringes are often made of stainless steel, and sometimes of aluminum or of synthetic resin. They are provided with respective endpieces of shape adapted to being inserted into a patient's mouth and pointed in an appropriate direction. The endpiece is removable but not consumable, so between two interventions, once it has been removed, it is therefore necessary for it to be cleaned and sterilized, with that naturally constituting a task that is expensive and time-consuming, while also being not entirely reliable as to its result.

Proposals have been made to replace the use of such a non-consumable endpiece that is difficult to clean and sterilize with the use of discardable endpieces for single use only that are easy to install on the syringe between two patients. The use of such endpieces has become much more widespread in recent years, thus enabling hygiene conditions to be improved to the benefit of patients and practitioners.

Thus, document WO 92/04878, which relates to the problem of reducing the cost of fabricating such discardable endpieces, describes an assembly made up of a cannula and a metal adapter that is suitable for connecting at a first end to a syringe of a given type and at a second end to a connection bushing of a discardable cannula made of molded plastics material. Male channels extending side by side project from the adapter and, during assembly, they are inserted into the openings of female channels in the cannula in order to deliver water and air thereto.

Those two parts, the cannula and the adapter, are oriented relative to each other by aligning an axial spline carried by the inside wall of the bushing of the cannula with a complementary slot formed in the outside wall of the adapter. Once positioned in this way, the parts are mutually engaged by being moved in translation, and after a short stroke the male channels engage in the female channels.

Nevertheless, that system presents the drawback whereby the initial positioning of the cannula and the syringe is essentially performed only by eye by aligning the spline with the slot. If they are aligned in approximate manner only and if the user applies pressure too quickly, the parts engage each other while they are slightly offset, thereby having the consequence of the male channels touching the walls of the female channels. This can lead to plastics material swarf being formed that might block the channels, and possibly also to deformation of a male channel, thereby leading to malfunction of the multifunction syringe.

Furthermore, that system assumes that the two portions (the cannula and the adapter) are a very good dimensional fit in order ensure that the pressure of the fluid does not cause the cannula to separate from and drop off the syringe, or even be swallowed by the patient. An alternative, described in document WO 92/04878 consists in providing a plurality of elastically deformable projections on the inside face of the connection bushing, which projections are received in a peripheral groove of the adapter. Nevertheless, that solution makes the cannula more complicated to put into place.

Finally, the system of document WO 92/04878 runs the risk of the male channels of the adapter being twisted when the cannula is removed. Given the need for the cannula to be securely fastened to the syringe, the user needs to exert a certain amount of force in order to remove the cannula. The user may be tempted to take hold of the tube close to the bushing and to twist it in order to increase grip on the cannula. This has the consequence of also twisting the male channels that are engaged in the female channels of the tube.

A cannula for a dental syringe is also known from document WO 90/07912, which cannula is suitable for being fastened on the syringe with the help of a bayonet type coupling carried by the syringe or by an adapter and projecting radially outwards. Such a bayonet coupling co-operates with an L-shaped track formed in the cannula. More precisely, the track has an inlet segment parallel to the longitudinal direction and a second segment extending at 90° to the inlet portion over an angular sector of the circumference of the cannula.

The practitioner assembles the bayonet coupling initially by moving the cannula and the syringe relative to each other in the longitudinal direction until coming into abutment against the intersection between the two segments of the track. Thereafter the cannula and the syringe are turned relative to each other to the end of the second segment.

It should be observed that that bayonet coupling system is not compatible with the channels of the cannula as described in document WO 92/04878 since with the channels arranged side by side in the cannula, the two parts need to be put into alignment before they move relative to each other in the longitudinal direction. Document WO 90/07912 provides for different channels that are compatible with the late turning that it proposes, since the two channels it describes are coaxial.

Nevertheless, the two channels are present only in the external portion of the cannula and not in the portion connected to the syringe and/or adapter, making it necessary to have a gasket in order to attempt to keep the air and water totally separate. Thus, depending on the positioning of the gasket, which may vary on each occasion a new cannula is put into place, and also depending on the aging state of the gasket, it can become impossible to obtain air that is completely dry. Unfortunately, such air that is completely dry is essential in performing certain acts of dentistry, and this therefore gives rise to a significant problem in use of that equipment.

SUMMARY OF THE INVENTION

In order to solve the various problems described above, there is provided a cannula for a multifunction dental syringe, the cannula comprising a fastener bushing that is defined by a circular opening, an end wall, and a side wall comprising a circular cylinder, the cannula also including at least two channels enabling fluids to be conveyed separately or together from said end wall to fluid projection orifices, the two channels beginning in said end wall beside each other, the cannula being characterized in that the circular cylinder includes a cutout in the thickness of the wall, which cutout includes at least one transverse segment starting from the opening (i.e. a segment arranged crosswise relative to the axis of the cylinder), in other words extending in a direction that is different from the direction of the axis of the cylinder, followed by a longitudinal segment that is parallel to the axis of the cylinder and that is directed towards the end wall.

The cutout in the thickness of the wall serves to receive a peg carried by the side wall of a fastening cylinder of the multifunction syringe or of the adapter. The longitudinal segment serves to guide turning of the cannula about the axis until the male channels carried by the syringe are perfectly positioned on the cylinder relative to the peg and are in alignment with the female channels in the cannula. This makes it possible to overcome potential poor verification by the user of how the parts are engaged together. Once the transverse segment has performed its guidance, the longitudinal segment enables the parts to be engaged until they are secured together. In summary, the male and female channels are brought into alignment by means that are mechanical, and therefore more reliable than the inspection by eye only of the prior art.

These characteristics avoid any plastics material swarf being formed while the cannula is being put into place, and also avoids any deformation of the channels projecting from the syringe. The working lifetime of the syringe is lengthened and the operations performed by the practitioner are simplified.

Finally, the qualities of the various fluids are fully complied with. The system is thus more reliable, more hygienic, simpler, and more reliable in use.

These advantages constitute a remarkable improvement over the disclosure of document WO 92/04878, which improvement could not be obtained on the basis of teaching available from elsewhere, and in particular on the basis of the teaching of document WO 90/07912. Specifically, WO 90/07912 proposes channels that are coaxial, which is very different from parallel channels opening out one beside the other in the cannula of the invention. Furthermore, WO 90/07912 does not propose an abutment position against movement in translation, nor does it propose two distinct abutment positions as in certain embodiments of the invention.

Advantageously, the cutout includes an abutment opposing movement in the direction away from the end wall.

By means of this abutment, any risk of the cannula becoming detached under the effect of the pressures generated by the fluid being projected is avoided, even if the manufacturing tolerances on the diameters of the bushing are high. This avoids any risk of the cannula being swallowed by the patient.

For example, the abutment against movement in translation comprises a local constriction in the cutout. Thus, the cannula is locked on the syringe and does not move while it is being used by the practitioner. This serves to facilitate fabrication since the tolerance on the diameter of the parts may be greater.

Preferably, the width of the cutout varies more abruptly beside the second position of the abutment against movement in translation relative to the local constriction than beside the opposite side. This makes it easier to put the cannula into place.

Advantageously, the cutout has an opening that is chamfered. This enables the adapter peg to be guided towards the inside of the cutout, even if the user aligns the parts poorly by manipulating them quickly.

Advantageously, the cannula includes reinforcement on the outside of the bushing in register with the opening of the cutout. Such reinforcement serves to guarantee mechanical cohesion of the part.

Also advantageously, the openings of the channels in said end wall are chamfered. Thus, if in spite of everything the male channels of the adapter are poorly positioned relative to the female channels of the cannula, mutual engagement is facilitated by the guidance provided by the chamfer.

In an advantageous embodiment, the channels are reinforced in the proximity of the bushing, e.g. by brackets. Thus, the male channels, once engaged in the female channels, do not risk being twisted by a user seeking to detach the cannula and twisting it in untimely manner: the brackets serve to prevent any such twisting.

In another advantageous aspect, the cannula includes a grip zone around a tube in which the channels are buried, providing a grip surface that is larger than provided by the tube on its own. Thus, when removing the cannula, the user applies force in controlled manner.

In a second aspect of the invention, there is provided an adapter for fastening a discardable cannula to the end of a multifunction dental syringe, the adapter having an end with the general shape of a circular cylinder terminating at a section from which at least two channels project beside each other, the adapter being characterized in that a peg projects locally from the side wall of the end. Such an adapter is used for fastening the above-mentioned discardable cannulas on a multifunction syringe.

BRIEF DESCRIPTION OF THE FIGURES

The present invention is described with reference to the following figures.

FIG. 5 is a detail view of the cutout of the bushing of the cannula of FIGS. 1 and 2.

FIG. 7 is a view of the cannula of FIGS. 1, 2, 5, and 6 from a different angle.

FIG. 9 is a section view of the cannula of FIGS. 1 to 7.

DETAILED DESCRIPTION OF THE INVENTION

Figure 1:
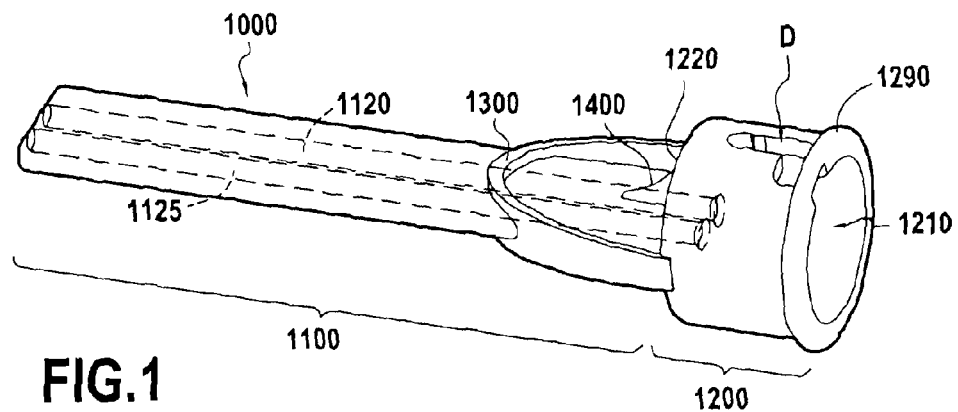
FIG. 1 is a three-quarter view of a cannula in an embodiment of the invention.

FIG. 1 shows a cannula 1000 in an embodiment of the invention. It is a molded plastics part with its various elements being made as a single piece. It is for fastening to a multifunction dental syringe, via an adapter. By way of example, its total length is about 5.5 centimeters (cm).

In a first approach, the cannula 1000 is made up of two major portions, namely a tube 1100 and a bushing 1200.

The tube 1100 is of elongate cylindrical shape. It is oblong in section, containing two parallel bores that run along its entire length, forming channels 1120 and 1125 for the fluids projected by the syringe. The channels are of similar diameters, and they are arranged side by side.

The end of the tube 1100 remote from the bushing 1200 is free and may be of rounded, chamfered shape (see the section of FIG. 9). Its surface constitutes a section of the tube 1100 that is inclined relative to its axis. It presents two orifices for projecting air and water as fluids from the cannula into the mouth of a patient. In certain embodiments, the channels 1120 and 1125 have a specific internal structure close to the projection orifices suitable for forming a combined air and water spray when air and water are projected together.

The bushing 1200 is generally in the form of a hollow circular cylinder having the same axis as the tube 1100 and having two ends of circular sections 1210 and 1220, the first being hollow and the second solid. The side wall of the bushing 1200 presents thickness of about 1 millimeter (mm), for example. The diameter of the bushing is slightly greater than 1 cm, it being possible for these dimensions to be varied.

The tube 1100 is fastened at right angles to the center of the section 1220 of the bushing 1200.

The cannula 1000 also presents reinforcement and engagement members given references 1290, 1300, and 1400, which elements are described with reference to the following figures. In remarkable manner, it presents a cutout D in the wall of the bushing. This cutout is described in greater detail below.

Figure 2:
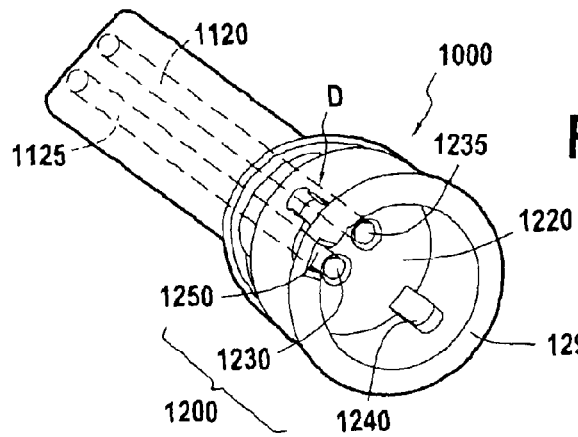
FIG. 2 is an inside view of the fastener bushing of the FIG. 1 cannula.

FIG. 2 shows the inside of the fastener bushing of the cannula 1000. It is seen looking through its open section 1210. The tube 1100 can be seen in the background.

The inside wall of the section 1220 is visible at the bottom of the bushing 1200. This wall 1220 is pierced by the openings 1230 and 1235 of the channels 1120 and 1125. These openings 1230 and 1235 are placed close to the center of the wall 1220, in register with the tube 1100.

Advantageously, the openings 1230 and 1235 are also chamfered, e.g. at angles of about 45°.

On the inside wall of the bushing 1200 there is a spline 1240 that acts as a keying member to make it easier to put the cannula into place on the syringe. The spline begins in contact with the wall 1220 and extends longitudinally, terminating about two-thirds of the way along the bushing 1200. The width of the spline 1240 is about 10°. It is terminated by a rounded end. It also presents a flat surface facing the axis of the bushing 1200.

In particularly remarkable manner, the side wall of the bushing 1200 presents a cutout D that passes radially therethrough. This cutout is restricted to a small angular sector of the bushing 1200, occupying about 20°. The beginning of the cutout D in the open section 1210 can be seen with reference 1250, designating the opening of the cutout in the open section 1210. On each side of this opening 1250, the wall of the bushing 1200 is chamfered, e.g. at an angle of 45°.

The precise shape of the cutout D is described in greater detail below with reference to the following figures.

Reinforcement 1290 that is shown as being perfectly circularly symmetrical in the embodiment described, is present on the outside surface of the bushing 1200 in register with the section 1210, in particular going over the opening 1250. The thickness of the reinforcement in the longitudinal direction may be about 1 mm, and in the radial direction it may be about 1 mm.

Figures 3, 4:
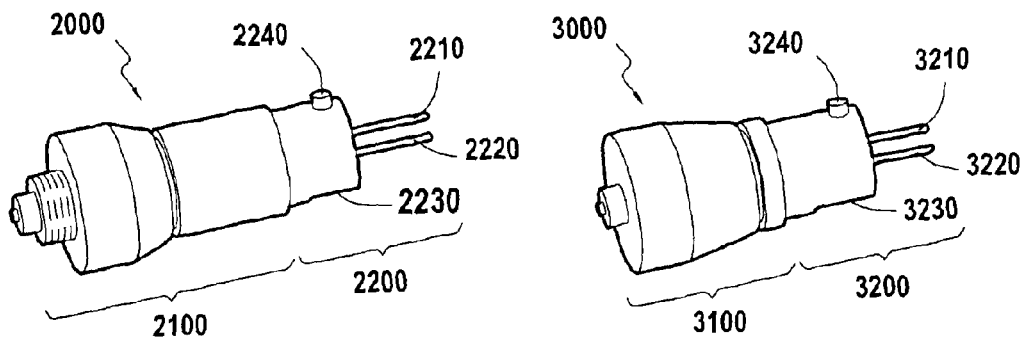
FIG. 3 is a view of a first embodiment of an adapter of the invention.
FIG. 4 is a view of a second embodiment of an adapter of the invention.

FIG. 3 shows a first embodiment of an adapter of the invention for co-operating with the cannula 1000 shown in FIGS. 1 and 2. The adapter is made of stainless steel, or of aluminum, or indeed of synthetic resin. It is made up of two sections that are arranged consecutively in a longitudinal direction.

A first section 2100 is a section for fastening to a multifunction dental syringe. It is specific to a given type of multifunction dental syringes, as provided by a given manufacturer of dentists' chairs.

The second section, referenced 2200 is a section for fastening to a cannula of the type shown in FIGS. 1 and 2. It is generally a body of revolution, being generally cylindrical in shape, with a free end constituting a right and plane section of the cylinder. Male metal channels project from this end and are suitable for engaging in the openings 1230 and 1235 of the channels in the cannula 1000. A longitudinal slot 2230 is adapted to receive the spline 1240 of the cannula 1000.

Finally, in remarkable manner, a peg 2240 projects locally over a given angular sector of the cylinder and radially from the wall of the section 2200. This peg 2240 is adapted to be engaged in the cutout D of the bushing 1200 via the opening 1250.

In FIG. 4, there can be seen an adapter 3000 in a second embodiment of the invention. In similar manner to the adapter 2000 shown in FIG. 3, this adapter 3000 has a first section 3100 for enabling it to be fastened to the end of a specific multifunction dental syringe supplied by a given dentists' chair manufacturer.

The adapter 3000 also has a section 3200 for fastening to the cannula 1000. The section 3200 is entirely similar to the section 2200 described with reference to FIG. 3.

Figure 6:
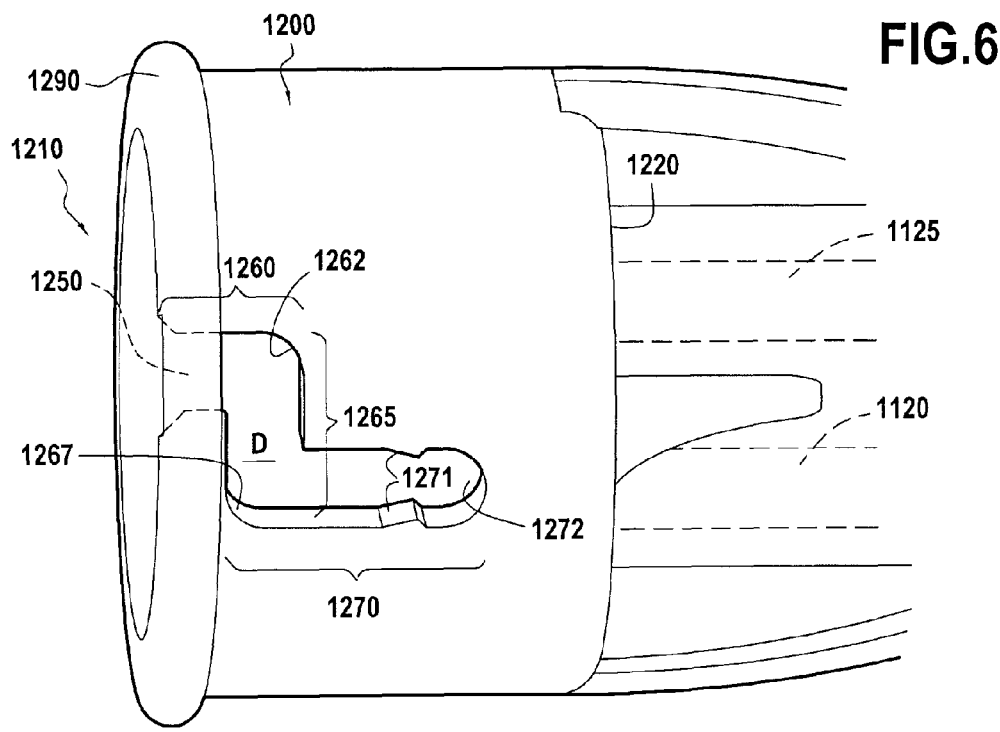
FIG. 6 is a second detail view of the same cutout.

With reference to FIGS. 5 and 6, there follows a description in detail of the shape of the cutout D present in the wall of the bushing 1200. This cutout is placed approximately diametrically opposite from the spline 1240.

This cutout D begins in the section 1210 via the opening 1250, and then has a first segment of constant width extending in the longitudinal direction of the bushing. This segment is referenced 1260 in FIG. 6. It is followed by a second segment 1265 at right angles to the first segment 1260, thus extending circumferentially relative to the bushing, over an angular sector of the bushing that occupies about ten degrees. This segment 1265 continues to be constant width. It is followed by a third elongate segment, referenced 1270, at right angles to the second segment and extending, like the first segment 1260, in the longitudinal direction, towards the tube 1100.

The third segment 1270 is of a length that is substantially twice the length of the first segment 1260. It is terminated by a blind end 1272. Over the major fraction of its length, the segment 1270 is of constant width. Nevertheless, on approaching the end 1272, it presents in its two walls two projections that give rise to a constriction in the width of the cutout at the location of the projection.

The angle 1262 between the segments 1260 and 1265 defines an abutment position, which is a position in abutment in translation for the peg 2240 or 3240 penetrating into the cutout when the practitioner places the cannula on the syringe. This abutment position makes it possible to keep out of engagement the male channels carried by the syringe or the adapter during initial engagement of the two parts, which could be poorly performed by the user, in particular in terms of angular alignment between the cannula and the syringe.

The angle 1267 between the segments 1265 and 1270 also defines an abutment position, which is a position in which the peg is prevented from moving in rotation while the cannula is put into place. This abutment position, representing the guidance function of the segments 1265, makes it possible to ensure that the cannula and the syringe are in angular alignment, and thus that the male and female channels are in angular alignment, with this being achieved mechanically in a manner that is more effective than the purely visual alignment of the prior art.

The segment 1270 enables the male channels to be inserted into the female channels, given that they are correctly positioned at this stage.

The angle 1267 between the segments 1265 and 1270 also defines an abutment position against movement in translation for the peg when separating the cannula 1000 from the syringe. This aspect constitutes a safety feature to prevent a poorly fitted cannula dropping into a patient's mouth under drive from the projected stream of liquid or air.

FIG. 7 shows the cannula 1000 in side view. There can be seen the tube 1100 and the bushing 1200. There follows a description of the engagement and reinforcing elements that can already be seen in the above-described figures.

The cannula 1000 advantageously has an arch 1300 stemming from two diametrically opposite points of the section 1220 of the bushing 1200. The arch 1300 defines a plane that is perpendicular to the section 1220. The long dimension of the section of the tube 1100 lies in this plane. The inside of the arch 1300 comprises a surface of material around the base of the tube 1100 that constitutes an additional grip for a user seeking to manipulate the cannula, and in particular to remove it from the syringe. The user may place a thumb on one side of the arch and a finger on the other side of the arch, thereby providing a large surface for gripping the cannula.

Two angle brackets 1400 are arranged perpendicularly to the plane of the arch 1300 between the tube 1100 and the wall of the section 1220. These brackets constitute reinforcements at the junction between the tube 1100 and the bushing 1200. They oppose twisting of the tube 1100 about an axis parallel to the long direction of its section. By way of example, the two brackets 1400 are arranged symmetrically to each other about the axis of the bushing.

The height of the arch 1300 is about one-fifth of the height of the tube 1100. The height of the bracket 1400 is about one-fourth of the height of the arch 1300. These proportions may be varied.

In a variant, the bushing 1200 is not constituted solely by a hollow cylinder, but also comprises, between the hollow cylinder and the tube 1100, a hollow truncated cone. Such a cone may match a complementary shape at the end of the adapter. The openings of the female channels are positioned in the end wall of the cone, and the male channels of the adapter are positioned at the end of complementary shape.

In another variant, possibly combinable with the above variant, the cutout in the wall of the cylinder does not pass through the wall but constitutes only a groove in the inside surface of the wall.

In another embodiment, the cutout is in the outside surface of the wall, and the cannula co-operates with an adapter having an additional outer cylinder that carries a peg that is inwardly directed.

Figure 8:
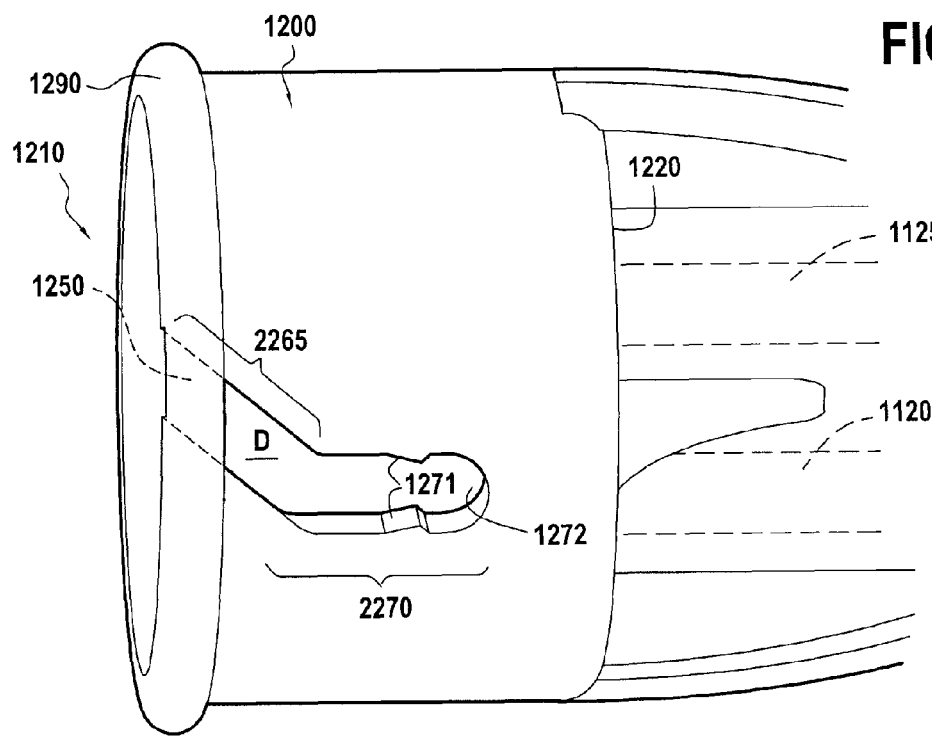
FIG. 8 shows a second embodiment of the invention.

Furthermore, in another embodiment of the cutout, as shown in FIG. 8, the cutout comprises only two segments: the segments 1260 and 1265 are replaced by a single segment 2265 running along the cylinder transversely but not perpendicularly to its axis, e.g. at an angle of 45°. Like the segment 1265 in the embodiment of FIG. 6, its function is to guide the cannula and the syringe in their angular movement relative to each other. A longitudinal segment 2270 similar to the segment 1270 then enables mutual engagement of the parts until they are secured to each other. The dimensions of the spline 1240 and of the slot 2230 are adapted to be compatible with the travel defined by the segments 2260 and 2270.

The invention is not limited to the embodiments described but extends to any variant within the ambit of the scope of the claims.

The invention claimed is:

1. A cannula for a multifunction dental syringe, the cannula comprising a fastener bushing that is defined by a circular opening, an end wall, and a side wall comprising a circular cylinder, the cannula also including at least two channels enabling fluids to be conveyed separately or together from said end wall to fluid projection orifices, the two channels beginning in said end wall beside each other, the cannula arranged so that the circular cylinder defines a cutout in the thickness of the side wall, which cutout comprises, going from the opening: at least one segment extending in a direction other than the axial direction of the cylinder; followed by a longitudinal segment extending towards the end wall.

2. A cannula according to claim 1, wherein the cutout includes an abutment adapted to oppose movement away from the end wall.

3. A cannula according to claim 2, wherein the abutment comprises a local constriction in the cutout.

4. A cannula according to claim 3, wherein the longitudinal segment is of constant width over a major fraction of a length of the longitudinal segment, but on approaching a blind end with which the longitudinal segment terminates, the longitudinal segment presents projections from two walls of the longitudinal segment that constrict the width of the cutout in register therewith, the width of the cutout varying more abruptly on an end wall side of the local constriction than on a side of the local construction opposite from the end wall side of the local constriction.

5. A cannula according to claim 1, wherein the cutout has an opening that is chamfered.

6. A cannula according to claim 1, including reinforcement on the outside of the bushing in register with the opening of the cutout.

7. A cannula according to claim 1, wherein the openings of the channels in said end wall are chamfered.

8. A cannula according to claim 1, wherein the channels are reinforced in the proximity of the bushing by brackets.

9. A cannula according to claim 1, including a grip zone in the proximity of the bushing around a tube in which the channels are buried, providing a grip surface that is larger than a surface provided by the tube.

* * * * *